(12) United States Patent
Hossainy et al.

(10) Patent No.: US 7,186,789 B2
(45) Date of Patent: Mar. 6, 2007

(54) BIOABSORBABLE, BIOBENEFICIAL POLYESTER POLYMERS FOR USE IN DRUG ELUTING STENT COATINGS

(75) Inventors: Syed F. A. Hossainy, Fremont, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 202 days.

(21) Appl. No.: 10/460,016

(22) Filed: Jun. 11, 2003

(65) Prior Publication Data
US 2004/0253203 A1    Dec. 16, 2004

(51) Int. Cl.
*C08G 63/00* (2006.01)
(52) U.S. Cl. .................. 528/272; 424/78.08; 528/271; 623/1.42; 623/1.46
(58) Field of Classification Search ............. 424/78.08; 528/271, 272; 623/1.42, 1.46
See application file for complete search history.

(56) References Cited

U.S. PATENT DOCUMENTS

| | | | |
|---|---|---|---|
| 3,839,743 A | 10/1974 | Schwarcz ........................... 3/1 |
| 3,900,632 A | 8/1975 | Robinson .................... 428/196 |
| 3,908,201 A | 9/1975 | Jones et al. |
| 4,110,497 A | 8/1978 | Hoel ........................... 428/190 |
| 4,321,711 A | 3/1982 | Mano .............................. 3/1.4 |
| 4,346,028 A | 8/1982 | Griffith ....................... 524/417 |
| 4,350,806 A | 9/1982 | Wagener |
| 4,633,873 A | 1/1987 | Dumican et al. ........... 128/334 |
| 4,656,083 A | 4/1987 | Hoffman et al. ............. 428/265 |
| 4,718,907 A | 1/1988 | Karwoski et al. ............. 623/12 |
| 4,722,335 A | 2/1988 | Vilasi .......................... 128/207 |
| 4,723,549 A | 2/1988 | Wholey et al. ............. 128/344 |
| 4,732,152 A | 3/1988 | Wallstén et al. ............ 128/343 |
| 4,733,665 A | 3/1988 | Palmaz ....................... 128/343 |
| 4,739,762 A | 4/1988 | Palmaz ....................... 128/343 |
| 4,740,207 A | 4/1988 | Kreamer ........................ 623/1 |
| 4,743,252 A | 5/1988 | Martin, Jr. et al. ............. 623/1 |
| 4,768,507 A | 9/1988 | Fischell et al. ............. 128/303 |
| 4,776,337 A | 10/1988 | Palmaz ....................... 128/343 |
| 4,816,339 A | 3/1989 | Tu et al. ..................... 428/421 |
| 4,850,999 A | 7/1989 | Planck ........................... 623/1 |
| 4,877,030 A | 10/1989 | Beck et al. ................. 128/343 |
| 4,878,906 A | 11/1989 | Lindemann et al. ........... 623/1 |
| 4,879,135 A | 11/1989 | Greco et al. ................... 427/2 |
| 4,902,289 A | 2/1990 | Yannas ........................... 623/1 |
| 4,977,901 A | 12/1990 | Ofstead ....................... 128/772 |
| 4,994,298 A | 2/1991 | Yasuda ......................... 427/41 |
| 5,019,090 A | 5/1991 | Pinchuk ..................... 606/194 |
| 5,028,597 A | 7/1991 | Kodama et al. .............. 514/56 |
| 5,059,211 A | 10/1991 | Stack et al. ................. 606/198 |
| 5,062,829 A | 11/1991 | Pryor et al. ................... 604/57 |
| 5,084,065 A | 1/1992 | Weldon et al. ................ 623/1 |
| 5,085,629 A | 2/1992 | Goldberg et al. .............. 604/8 |
| 5,100,429 A | 3/1992 | Sinofsky et al. ............ 606/195 |
| 5,108,755 A | 4/1992 | Daniels et al. .............. 424/426 |
| 5,112,457 A | 5/1992 | Marchant .................... 204/165 |
| 5,123,917 A | 6/1992 | Lee ................................ 623/1 |
| 5,156,623 A | 10/1992 | Hakamatsuka et al. ....... 623/11 |
| 5,163,951 A | 11/1992 | Pinchuk et al. ................ 623/1 |
| 5,163,952 A | 11/1992 | Froix ............................. 623/1 |
| 5,163,958 A | 11/1992 | Pinchuk ....................... 623/11 |
| 5,167,614 A | 12/1992 | Tessmann et al. ............. 604/8 |
| 5,192,311 A | 3/1993 | King et al. .................... 623/1 |
| 5,197,977 A | 3/1993 | Hoffman, Jr. et al. .......... 623/1 |
| 5,234,456 A | 8/1993 | Silvestrini .................. 606/194 |
| 5,234,457 A | 8/1993 | Andersen ................... 606/198 |
| 5,236,447 A | 8/1993 | Kubo et al. .................... 623/1 |
| 5,279,594 A | 1/1994 | Jackson ...................... 604/265 |
| 5,282,860 A | 2/1994 | Matsuno et al. .............. 623/12 |
| 5,289,831 A | 3/1994 | Bosley ........................ 128/899 |
| 5,290,271 A | 3/1994 | Jernberg ................... 604/891.1 |
| 5,306,286 A | 4/1994 | Stack et al. ................. 606/198 |
| 5,306,294 A | 4/1994 | Winston et al. ................ 623/1 |
| 5,328,471 A | 7/1994 | Slepian ....................... 604/101 |
| 5,330,500 A | 7/1994 | Song .......................... 606/198 |
| 5,342,348 A | 8/1994 | Kaplan ..................... 604/891.1 |
| 5,342,395 A | 8/1994 | Jarrett et al. ................. 606/219 |
| 5,342,621 A | 8/1994 | Eury .......................... 424/423 |
| 5,356,433 A | 10/1994 | Rowland et al. .............. 623/11 |
| 5,383,925 A | 1/1995 | Schmitt ......................... 623/1 |
| 5,385,580 A | 1/1995 | Schmitt ......................... 623/1 |
| 5,389,106 A | 2/1995 | Tower ........................ 606/198 |
| 5,441,515 A | 8/1995 | Khosravi et al. ........... 606/194 |
| 5,443,458 A | 8/1995 | Eury ....................... 604/891.1 |

(Continued)

FOREIGN PATENT DOCUMENTS

DE         44 07 079         9/1994

(Continued)

OTHER PUBLICATIONS

International Search Report and Written Opinion for application PCT/US 2004/015446, filed May 17, 2004, mailed Nov. 3, 2004, 22 pgs.

(Continued)

*Primary Examiner*—Terressa Boykin
(74) *Attorney, Agent, or Firm*—Squire, Sanders & Dempsey L.L.P.

(57) ABSTRACT

This disclosure covers polymers, some of which are useful in medical device applications. Some of these medical devices are implantable within a mammalian body, such as in a body lumen. The copolymers comprise at least one alcoholic moiety derived from a diol, triol, or polyol. Additionally, the copolymers comprise an acidic moiety, derived from a polycarboxylic acid, and a biobeneficial moiety. Some of these copolymers are biodegradable or bioerodable. Medical devices comprising these polymers and methods of making these polymers are within the scope of this disclosure.

42 Claims, No Drawings

U.S. PATENT DOCUMENTS

| | | | |
|---|---|---|---|
| 5,455,040 A | 10/1995 | Marchant | 424/426 |
| 5,464,650 A | 11/1995 | Berg et al. | 427/2.3 |
| 5,502,158 A | 3/1996 | Sinclair et al. | 528/354 |
| 5,514,379 A | 5/1996 | Weissleder et al. | 424/426 |
| 5,527,337 A | 6/1996 | Stack et al. | 606/198 |
| 5,554,120 A | 9/1996 | Chen et al. | 604/96 |
| 5,578,073 A | 11/1996 | Haimovich et al. | 623/1 |
| 5,591,607 A | 1/1997 | Gryaznov et al. | 435/91.1 |
| 5,593,403 A | 1/1997 | Buscemi | 606/2 |
| 5,599,301 A | 2/1997 | Jacobs et al. | 604/65 |
| 5,599,922 A | 2/1997 | Gryaznov et al. | 536/25.3 |
| 5,605,696 A | 2/1997 | Eury et al. | 424/423 |
| 5,629,077 A | 5/1997 | Turnlund et al. | 442/38 |
| 5,631,135 A | 5/1997 | Gryaznov et al. | 435/6 |
| 5,637,113 A | 6/1997 | Tartaglia et al. | 623/1 |
| 5,667,767 A | 9/1997 | Greff et al. | 424/9.411 |
| 5,670,558 A | 9/1997 | Onishi et al. | 523/112 |
| 5,693,085 A | 12/1997 | Buirge et al. | 623/1 |
| 5,700,286 A | 12/1997 | Tartaglia et al. | 623/1 |
| 5,707,385 A | 1/1998 | Williams | 606/192 |
| 5,716,981 A | 2/1998 | Hunter et al. | 514/449 |
| 5,726,297 A | 3/1998 | Gryaznov et al. | 536/22.1 |
| 5,728,751 A | 3/1998 | Patnaik | 523/112 |
| 5,733,925 A | 3/1998 | Kunz et al. | 514/449 |
| 5,741,881 A | 4/1998 | Patnaik | 528/75 |
| 5,756,476 A | 5/1998 | Epstein et al. | 514/44 |
| 5,756,477 A | 5/1998 | Hovanessian et al. | 514/44 |
| 5,766,710 A | 6/1998 | Turnlund et al. | 428/36.1 |
| 5,779,729 A | 7/1998 | Severini | |
| 5,800,516 A | 9/1998 | Fine et al. | 623/1 |
| 5,811,447 A | 9/1998 | Kunz et al. | 514/411 |
| 5,824,049 A | 10/1998 | Ragheb et al. | 623/1 |
| 5,830,178 A | 11/1998 | Jones et al. | 604/49 |
| 5,830,461 A | 11/1998 | Billiar | 424/94.4 |
| 5,830,879 A | 11/1998 | Isner | 514/44 |
| 5,833,651 A | 11/1998 | Donovan et al. | 604/53 |
| 5,834,582 A | 11/1998 | Sinclair et al. | 528/354 |
| 5,837,313 A | 11/1998 | Ding et al. | 427/2.21 |
| 5,837,835 A | 11/1998 | Gryaznov et al. | 536/23.1 |
| 5,851,508 A | 12/1998 | Greff et al. | 424/9.411 |
| 5,854,207 A | 12/1998 | Lee et al. | 514/2 |
| 5,854,368 A | 12/1998 | Iritani et al. | |
| 5,855,618 A | 1/1999 | Patnaik et al. | 623/11 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,874,165 A | 2/1999 | Drumheller | 428/308.4 |
| 5,876,743 A | 3/1999 | Ibsen et al. | 424/426 |
| 5,877,263 A | 3/1999 | Patnaik et al. | 525/453 |
| 5,879,713 A | 3/1999 | Roth et al. | 424/489 |
| 5,891,192 A | 4/1999 | Murayama et al. | 623/1 |
| 5,897,955 A | 4/1999 | Drumheller | 428/422 |
| 5,914,182 A | 6/1999 | Drumheller | 428/308.4 |
| 5,916,870 A | 6/1999 | Lee et al. | 514/2 |
| 5,942,209 A | 8/1999 | Leavitt et al. | 424/1.25 |
| 5,948,428 A | 9/1999 | Lee et al. | 424/426 |
| 5,957,975 A | 9/1999 | Lafont et al. | 623/1 |
| 5,965,720 A | 10/1999 | Gryaznov et al. | 536/23.1 |
| 5,971,954 A | 10/1999 | Conway et al. | 604/96 |
| 5,980,564 A | 11/1999 | Stinson | 623/1 |
| 5,980,928 A | 11/1999 | Terry | 424/427 |
| 5,980,972 A | 11/1999 | Ding | 427/2.24 |
| 5,981,568 A | 11/1999 | Kunz et al. | 514/411 |
| 5,997,468 A | 12/1999 | Wolff et al. | 600/36 |
| 6,015,541 A | 1/2000 | Greff et al. | 424/1.25 |
| 6,042,875 A | 3/2000 | Ding et al. | 427/2.24 |
| 6,048,964 A | 4/2000 | Lee et al. | 530/350 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,071,266 A | 6/2000 | Kelley | 604/265 |
| 6,074,659 A | 6/2000 | Kunz et al. | 424/423 |
| 6,080,177 A | 6/2000 | Igaki et al. | 606/198 |
| 6,080,488 A | 6/2000 | Hostettler et al. | 428/423.3 |
| 6,093,463 A | 7/2000 | Thakrar | 428/36.9 |
| 6,096,070 A | 8/2000 | Ragheb et al. | 623/1 |
| 6,096,525 A | 8/2000 | Patnaik | 435/181 |
| 6,099,562 A | 8/2000 | Ding et al. | 623/1.46 |
| 6,103,230 A | 8/2000 | Billiar et al. | 424/94.4 |
| 6,107,416 A | 8/2000 | Patnaik et al. | 525/453 |
| 6,110,188 A | 8/2000 | Narciso, Jr. | 606/153 |
| 6,113,629 A | 9/2000 | Ken | 623/1.1 |
| 6,117,979 A | 9/2000 | Hendriks et al. | 530/356 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,127,173 A | 10/2000 | Eckstein et al. | 435/320.1 |
| 6,129,761 A | 10/2000 | Hubbell | 623/11 |
| 6,153,252 A | 11/2000 | Hossainy et al. | 427/2.3 |
| 6,159,951 A | 12/2000 | Karpeisky et al. | 514/45 |
| 6,165,212 A | 12/2000 | Dereume et al. | 623/1.13 |
| 6,166,130 A | 12/2000 | Rhee et al. | 525/54.1 |
| 6,169,170 B1 | 1/2001 | Gryaznov et al. | 536/23.1 |
| 6,171,609 B1 | 1/2001 | Kunz | 424/422 |
| 6,174,330 B1 | 1/2001 | Stinson | 623/1.34 |
| 6,177,523 B1 | 1/2001 | Reich et al. | 525/459 |
| 6,224,626 B1 | 5/2001 | Steinke | 623/1.16 |
| 6,228,845 B1 | 5/2001 | Donovan et al. | 514/44 |
| 6,245,103 B1 | 6/2001 | Stinson | 623/1.22 |
| 6,251,135 B1 | 6/2001 | Stinson et al. | 623/1.34 |
| 6,251,142 B1 | 6/2001 | Bernacca et al. | 623/23.57 |
| 6,861,482 B2 * | 3/2005 | Brunelle et al. | 525/439 |

FOREIGN PATENT DOCUMENTS

| | | |
|---|---|---|
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 759 459 | 2/1997 |
| EP | 0 797 963 | 10/1997 |
| EP | 0 970 711 | 1/2000 |
| EP | 0 987 284 | 3/2000 |
| EP | 1 038 538 | 9/2000 |
| GB | 2 247 696 | 3/1992 |
| JP | 07-330954 | 12/1995 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 95/29647 | 11/1995 |
| WO | WO 97/47670 | 12/1997 |
| WO | WO 99/34750 | 7/1999 |
| WO | WO 99/55760 | 11/1999 |
| WO | WO 00/12147 | 3/2000 |
| WO | WO 00/44309 | 8/2000 |
| WO | WO 00/62630 | 10/2000 |
| WO | WO 00/64506 | 11/2000 |
| WO | WO 00/74744 | 12/2000 |
| WO | WO 00/77069 | 12/2000 |

| WO | WO 01/01890 | 1/2001 |

OTHER PUBLICATIONS

Bonzon et al., "New bioactivation mode for vascular prostheses made of Dacron® polyester", Biomaterials vol. 16, No. 10, (1995), pp. 747-751.

S.-G. Hu et al., "Surface Grafting of Polyester Fiber with Chitosan and the Antibacterial Activity of Pathogenic Bacteria", J. of Applied Polymer Science, vol. 86, (2002), pp. 2977-2983.

Yan Liu et al., "New Biodegradable Polymers from Renewable Sources", Rapra Abstracts, Journal of Bioactive & Compatible Polymers, vol. 17, No. 3, (2002), 1 pg.

Nouaimi et al., "Immobilization of trypsin on polyester fleece via different spacers", Enzyme and Microbial Technology 29, (2001), pp. 567-574.

Strecker et al., "The Determination of Reactive-Group Functionality from Gel Point Measurements", J. of Applied Polymer Science vol. 12, (1968), pp. 1697-1712.

Sepulchre et al., "Water-soluble polymers bearing biologically active residues, 1". Macromolecular Chemistry and Physics 194, Apr. 1993, No. 4, pp. 1065-1077.

Bull, *Parylene Coating for Medical Applications*, Medical Product Manufacturing News (1993).

Casper et al., *Fiber-Reinforced Absorbable Composite for Orthopedic Surgery*, Polymeric Materials Science and Engineering, 53:497-501 (1985).

Devanathan et al., *Polymeric Conformal Coatings for Implantable Electronic Devices*, IEEE Transactions on Biomedical Engineering, vol. BME-27(11):671-675 (1980).

Hahn et al., *Biocompatibility of Glow-Discharge-Polymerized Films and Vacuum-Deposited Parylene*, J Applied Polymer Sci, 38:55-64 (1984).

Hahn et al., *Glow Discharge Polymers as Coatings for Implanted Devices*, ISA, pp. 109-111 (1981).

Kelley et al., *Totally Resorbable High-Strength Composite Material*, Advances in Biomedical Polymers, 35:75-85 (1987).

Kubies et al., *Microdomain Structure In Polylactide-block-poly(ethylene oxide) Copolymer Films*, Biomaterials 21:529-536 (2000).

Muller et al., *Advances in Coronary Angioplasty: Endovascular Stents*, Coron Arter Dis, 1(4):438-448 (1998).

Nichols et al., *Electrical Insulation of Implantable Devices by Composite Polymer Coatings*, ISA Transactions, 26(4):15-18 (1987).

Schatz, *A View of Vascular Stents*, Circulation, 79(2):445-457 (1989).

Schmidt et al., *Long-Term Implants of Parylene-C Coated Microelectrodes*, Med & Biol Eng & Comp, 26(1):96-101 (1988).

* cited by examiner

BIOABSORBABLE, BIOBENEFICIAL POLYESTER POLYMERS FOR USE IN DRUG ELUTING STENT COATINGS

BACKGROUND

A current paradigm in biomaterials research is the control of protein adsorption on the surface of implantable medical devices. Uncontrolled protein adsorption, leading to a mixed layer of partially denatured proteins, is a hallmark of current biomaterials when implanted. Current surfaces present different cell binding sites from adsorbed plasma proteins such as fibrinogen and immunoglobulin G. Platelets and inflammatory cells such as monocyte/macrophages and neutrophils adhere to these surfaces. When so activated, they secret a wide variety of pro-inflammatory and proliferative factors. These unfavorable events can be controlled by the use of non-fouling surfaces. Non-fouling surfaces are surfaces that absorb little or no protein, primarily due to their hydrophilic surface properties. One prior art approach is to use hyaluronic acid and polyethylene glycol to provide this non-fouling surface characteristic. Biobeneficial coatings are surface coatings that are intended to provide a biological benefit without releasing pharmaceutically active agents. Another type of biobeneficial coating contains free radical scavengers to preserve nitric oxide and prevent oxidative damage.

Langer et al. have published a type of bioabsorbable, polyester polymer that they have dubbed "Biorubber". (Nature Biotechnology, vol. 20, p. 602, June 2002) This polymer is a polyester copolymer composed of sebacic acid and glycerol. It is a crosslinked elastomer, but possesses no biobeneficial or bioactive moieties. Improved polymers with non-fouling surfaces or with biobeneficial surfaces remain a goal in this art.

SUMMARY

This invention relates to copolymers, some of which are useful in medical device applications. Some of these medical devices are implantable within a mammalian body, such as in a body lumen. The copolymers comprise at least one alcoholic moiety derived from a diol, triol, or polyol. Additionally, the copolymers comprise an acidic moiety, derived from a polycarboxylic acid, and a biobeneficial moiety. Some of these copolymers are biodegradable or bioerodable. Medical devices comprising these polymers and methods of making other polymers are within the scope of this invention.

DETAILED DESCRIPTION

A family of bioabsorbable, non-fouling (biobeneficial) polyester polymers is disclosed. In some embodiments, these polymers compose the base material for implantable medical devices. In some embodiments, implantable medical devices comprise these polymers. And in some embodiments, these polymers compose implantable medical device coatings. This family of polymers comprises the following basic components:

(1) moieties derived from aliphatic diols, triols, or polyols;
(2) moieties derived from polycarboxylic acids (carboxylic acids containing more than one acid functionality); and
(3) biobeneficial, non-fouling, or bioactive moieties.

Some invention embodiments are block copolymers of one or more diols, triols, or polyols with a toxicologically acceptable acid monomer (polycarboxylic acid) such as the following: $C_2$ to $C_{12}$ straight chain, aliphatic diacids, specifically oxalic acid, malonic acid, succinic acid, glutaric acid, adipic acid, pimelic acid, suberic acid, azaleic acid, and sebacic acid. Longer chain lengths, such as found in dodecandioic acid, tetradecandioic acid, and hexadecandioic acid, are also possible. Polycarboxylic acids include citric acid and tartaric acid. Unsaturated polycarboxylic acids include fumaric acid and muconic acid. Lastly, useful aromatic polycarboxylic acids include terephthalic acid, isophthalic acid, phthalic acid, 1,6-bis(p-carboxy phenoxy)hexane, 1,3-bis(p-phenoxy carboxy)propane, and 1,4-bis(p-phenoxy carboxy)butane. In some invention embodiments, the toxicologically acceptable polycarboxylic acid monomer specifically excludes sebacic acid.

Some invention block copolymers can be represented by the following formula: $[AB]_n[A'B']_m$. In this formula A represents a moiety derived from an aliphatic diol, triol, or polyol. B represents a moiety derived from a polycarboxylic acid. In some embodiments these are limited to a toxicologically acceptable polycarboxylic acid monomer; in these or other embodiments, polycarboxylic acid monomers are selected from those specifically disclosed above. A' represents a moiety derived from an aliphatic diol, triol, or polyol that is the same as or different from A. And B' represents a moiety derived from a polycarboxylic acid that is the same as or different from B. n and m represent the relative length of each block in this block copolymer.

For purposes of this disclosure we define the soft block as having lower $T_g$ or being highly water swellable. In some embodiments, the block labeled "n" contains the BB moiety and is, therefore the soft segment or soft block because most biobeneficial moieties are hydrophilic and absorb water. The other block, labeled by "m", is referred to as the hard segment. For purposes of this disclosure, we define the hard blocks as the blocks with a lower water absorption or a higher $T_g$.

Invention copolymers can be linear or branched and can be crosslinked when desired. In some instances, crosslinking occurs through functional groups pendant from the polymer backbone. For instance, in some embodiments, the functional groups from acids in the backbone can serve as the crosslinking site. In other embodiments, the unsaturation in an unsaturated diacid serves as the crosslinking site. In yet other embodiments, hydroxyl groups are pendant from the polymer backbone and serve as the crosslinking site. Those of ordinary skill in the art will recognize that other ways of achieving crosslinks between polymer chains can be applied to invention copolymers. For example, to UV crosslink the polymers, some embodiments have UV polymerizable groups in the monomers. Such groups are typically acrylates or methacrylates. The general scheme would include replacing the hydroxyl and carboxylic acid groups with acrylate or methacrylate. This gives rise to another class of polymers.

Some invention block copolymers can be represented by the following formulas:

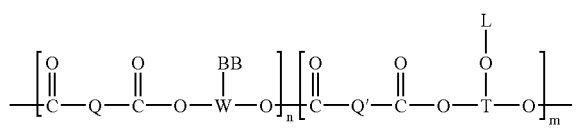

-continued

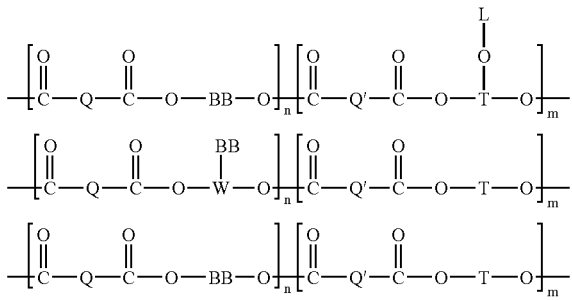

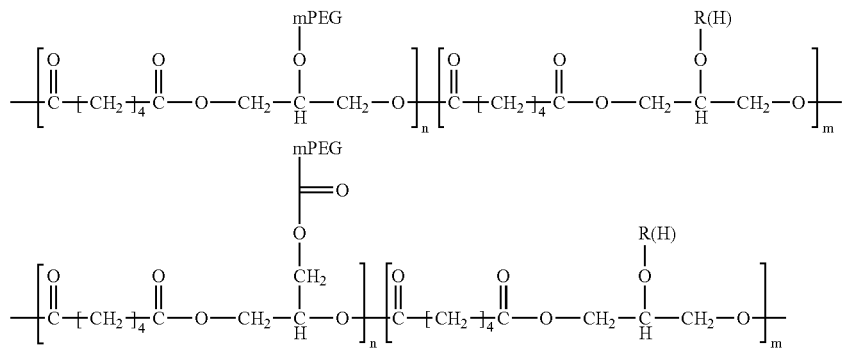

-continued

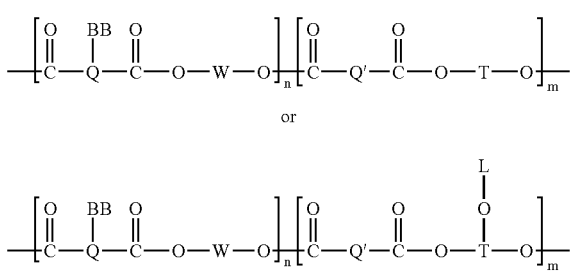

or

In these formulas, Q represents a 1–18 carbon-atom hydrocarbon chain; W represents a 1–8 carbon-atom hydrocarbon chain; T represents a 1–16 carbon-atom hydrocarbon chain; and BB represents a biobeneficial moiety. For purposes of this disclosure, hydrocarbon chains are defined as chains containing 1–50 carbon atoms and include straight and branched alkyl chains, chains containing pendant or in-chain rings, chains containing pendant or in-chain rings and alky substitutions, and chains containing aromatic groups and alkyl substitutions. Suitable substituted hydrocarbyl chains are hydrocarbyl chains as defined above that are independently substituted with one or more halogen, amido, phosphido, alkoxy, ether, sulfide, phosphate ester, or other Lewis acidic or basic functionality. n and m represent the length of the blocks. In some embodiments, n takes any value from 2 to 1250. In some embodiments, m takes any value from 10 to 4500. n:m is usually within 1:2250 to 125:1. This means that in some embodiments the m-block is 2250 repeat units long while the n-block is 1 repeat unit long. Finally, L represents a crosslinking group for those blocks containing a crosslink, and L represents hydrogen for those blocks not containing a crosslink.

In the above formulas, a —$CH_2$— group can be substituted with a —$Si(OR)_2$— group in which R is an alkyl, phenyl, or halogenated alkyl containing 1–6 carbon atoms. A —$CH_2$— group can be substituted with a keto group, C=O. And sulfur can be substituted for oxygen, thereby converting ether linkages into sulfide linkages.

In some embodiments, the block copolymer may comprise non-fouling or biobeneficial moieties. The formulas shown below represent two specific classes of invention polymers.

This polymer is comprised of moieties derived from glycerol, adipic acid, and mPEG. The diblock structure indicates that not all of the glycerol is derivatized with mPEG. A portion of the glycerol-derived moiety is involved in an ester crosslink as indicated by (R) or has a free hydroxyl as indicated by (H). In this structure, the PEG is pendant, but it can also be in the polymer backbone.

Diol, Triol, or Polyol

The diol, triol, or polyol component is a chain with one or more alcohol functionalities. In some embodiments this component is a mixture of di- or multi-alcoholic molecules such as mixtures with PEG diols, glycerol, other triols, etc. In some embodiments, this component is a mixture comprising PEG diols, PLURONIC (TM) diols, or glycerol or other triols.

In the diol, triol, or polyol, at least one hydroxy group should be present in order to form the hydrolyzable ester linkage. The hydrocarbyl groups T and W may have unsaturation. In polymer precursors containing groups T and W, sulfhydryl and amino groups can substitute for hydroxyl groups as long as at least one hydroxyl group remains to form an ester bond.

Here is a polymer with a sulfhydryl group substitution: one using mercaptoethanol, sebacic acid, and PEG300.

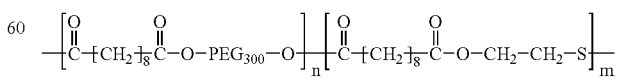

Criteria for choosing the polyol component depends on whether the component is for hydrocarbyl group T or group W. In addition to two hydroxyl groups, in order to be a part of the polymer backbone, group W requires a third, pendant functionality to attach to the biobeneficial moiety. If group T is to have a pendant hydroxyl or alkoxy group, it must also have this third functionality. However, when group T does not have or is not desired to have any pendant functional groups, it can be difunctional. In some embodiments having excellent biocompatibility, the polyol or polyols are endogenous or have established biocompatibilities.

Suitable polyols are ethylene glycol, 1,2-propane diol, 1,3-propane diol, 1,4-butanediol, 1,5-butanediol, 1,6-hexanediol, 1,7-heptanediol, 1,8-octanediol, higher diols up to $C_{16}$, glycerol, trimethylol propane, pentaerythritol, cyclohexanedimethanol, serinol, diethanolamine, and saccharides such as erythrose, threose, ribose, arabinose, xylose, lyxose, dihydroxyacetone, erythrulose, xylulose, aldoses, and ketoses. In some embodiments, polyols are 1,2-propanediol, 1,3-propanediol, 1,4-butanediol, 1,6-hexanediol, 1,10-decanediol, 1,12-dodecanediol, glycerol, serinol, diethanolamine, trimethylol propane, or pentaerythritol.

One embodiment uses phosphoryl choline-co-HEMA a biobeneficial, methacrylate copolymer. In this polymer, the phosporyl choline group is attached to a methacrylate. These polymers are not usually hydroxy terminated, but certain living polymerization schemes will function with these hydroxy terminated polymer.

Tri- or multi-functional —OH can copolymerize in the backbone such that two of the hydroxyl groups act to incorporate the polyol chain into the polymer. This leaves one or more remaining hydroxyl groups to conjugate a bioactive moiety. Or, one or more of the remaining hydroxyl groupscan serve as a crosslinking site.

Polycarboxylic Acid

The polycarboxylic acid is a compound with at least two carboxylic acid groups. For implant use, polycarboxylic acid used in this invention should be toxicologically acceptable. This means the toxicity it imparts to the polymer, and the toxicity of the monomer itself when released, should be low enough that the polymer can be used within a mammalian body. Specific examples of these include $C_2$ to $C_{12}$ straight chain aliphatic diacids, specifically oxalic acid, malonic acid, succinic acid, glutaric acid, adipic acid, pimelic acid, suberic acid, azelaic acid, sebacic acid, and citramalic acid. Longer chain lengths, such as found in dodecanedioic acid, tetradecanedioic acid, and hexadecanedioic acid, are useful in the practice of this invention. Polycarboxylic acids include citric acid, tricarballylic acid, and tartaric acid. Unsaturated polycarboxylic acids include fumaric acid and muconic acid. Lastly, useful aromatic polycarboxylic acids include terephthalic acid, isophthalic acid, phthalic acid, 1,6-bis(p-carboxy phenoxy)hexane, 1,3-bis(p-phenoxy carboxy)propane, and 1,4-bis(p-phenoxy carboxy)butane.

Specific examples of polycarboxylic acids include oxalic acid, malonic acid, succinic acid, glutaric acid, adipic acid, pimelic acid, suberic acid, azelaic acid, sebacic acid, terephthalic acid, and citric acid. Particularly suitable examples include succinic acid, adipic acid, sebacic acid, tricarballylic acid, citric acid, fumaric acid, terephthalic acid, and 1,3-bis(p-phenoxy carboxy)propane.

Biobeneficial Moiety

For purposes of this disclosure, the term "biobeneficial" is an umbrella description for any surface that provides biological benefit for an implantable medical device without the release of a pharmacologically active agent. Following this definition of "biobeneficial", the term biobeneficial moiety is a moiety that imparts, either by itself or with another moiety, to a polymer or surface the characteristic of being "biobeneficial". Within this umbrella definition, some surfaces may be regarded as non-fouling and some as bioactive, whereas others may be regarded as hemocompatible or non-thrombogenic. Also, biobeneficial moieties include moieties that have any combination of bioactive, non-fouling, or hemocompatible characteristics.

Biobeneficial moieties that are primarily non-fouling are poly(ethylene glycol), polypropylene glycol, PLURONIC (™) surfactants—block copolymers of polyethylene glycol and polypropylene glycol, hydroxy functional poly(vinyl pyrrolidone)dextran, dextrin, sodium hyaluronate, hyaluronic acid, elastin, chitosan, water-soluble chitosan, water-soluble heparin, water-soluble elastin, tropoelastin, Albumin, and poly(2-hydroxyethyl methylmethacrylate). Biobeneficial moieties that are primarily hemocompatible are heparin, hirudin, and sulfonated polystyrene. Particular bioactive agents would include superoxide dismutase mimetics, anti-oxidants, and free radical scavengers. Biobeneficial moieties can possess a combination of these or other properties.

A caveat is that the maximum molecular weight of this component should be low enough so that the released molecule can pass through the kidneys, e.g., in some embodiments the maximum molecular weight of this component is less than or equal to 40,000 Daltons, if the polymer is not absorbable by hydrolysis or enzymolysis. In this respect, a maximum molecular weight of 20,000 Daltons is more preferred. If the biobeneficial moiety itself is hydrolyzed or metabolized by the body, as would be the case with heparin, then the maximum molecular weight could be larger than the renal passage cutoff of approximately 40,000 Daltons.

Invention polymers can be linear or crosslinked. The biobeneficial components can be pendant or in the polymer backbone. A polymer of this invention can contain more than one type of biobeneficial moiety. For example, a non-fouling moiety can be pendant on select repeat units designated by "n" while a bioactive moiety could be present on other repeat units designated by "m". Bioactive moieties can be selected from PEG diols with molecular weights from 300–30,000.

The choice of values for "n" and "m" determines the total weight fraction of each block in the final polymer. For linear polymers there are limits to the amount of biobeneficial moiety that can be incorporated while retaining acceptable mechanical properties. For example, the non-fouling biobeneficial moieties are largely very hydrophilic and many are water-soluble. If the weight fraction of non-fouling component moieties becomes greater than approximately 80% by weight, then the linear polymer can swell excessively, or even dissolve, in water. Therefore, the weight fraction of non-fouling component moieties is chosen to be less than approximately 80 percent by weight in some embodiments. But if the weight fraction of the non-fouling moiety is too low, not enough will be present to modify the surface properties of the polymer. This level depends of the particular polymer, but is in the range of 1–10 percent by weight, below which biobeneficial, non-fouling properties will be subtle. Therefore, the weight fraction of non-fouling component moieties is chosen to be greater than 1–10 percent by weight in some embodiments. In the case of crosslinked systems, the problems of polymer dissolution are eliminated. Excessive swelling can still occur, which can weaken the polymer coating in some embodiments. In the case of hemocompatible, biobeneficial moieties, similar concerns apply because larger amounts of these moieties give higher surface concentrations at the expense of mechanical properties due to excessive water swelling.

Bioactive, biobeneficial moieties are not necessarily hydrophilic. In some embodiments, as much hemocompatible, biobeneficial moiety is incorporated into the polymer as can be incorporated into the polymer and still have the polymer retain acceptable mechanical properties for use in medial devices. For some embodiments, appropriate values of n are between 2 and 1250. For some embodiments, appropriate values of m are between 10 and 4500.

One specific embodiment of invention copolymers is the crosslinked terpolymer of glycerol, sebacic acid, and polyethylene glycol (PEG300). This polymer has the structure shown below.

amine-terminated mPEG (such as available from Nektar, formerly Shearwater Polymers) to tricarballylic acid via carbodiimide chemistry. This mPEG-derivatized diacid is then combined with the desired amount of 1,4-butanediol and succinic acid in a 1:1 mole ratio. Instead of ester formation via dehydration using heat and vacuum, further addition of an appropriate carbodiimide, such as 1-(3-dimethylaminopropyl)-3-ethylcarbodiimide hydrochloride (EDC) or 1,3-dicyclohexylcarbodiimide (DCC), will couple the carboxylic acid and hydroxyl groups to form the polyester. In some embodiments, this yields a linear polymer that

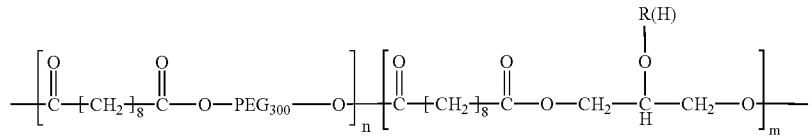

The reactivities of PEG300 and glycerol are quite different, so it is advantageous to produce this polymer in a two-step process. Generally, one equivalent of PEG300 is combined with two equivalents of sebacic acid. This is heated under vacuum to produce a sebacic-acid-terminated is solvent soluble and amenable to current stent coating processes.

Another specific embodiment of invention copolymers is a terpolymer of 1,3-propanediol, adipic acid, and PEG600. This polymer has the following structure.

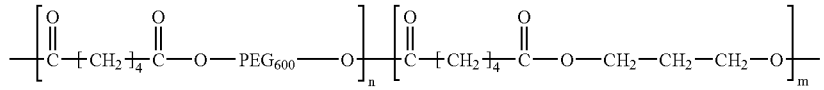

PEG300. Useful reaction temperatures range from 80 to 140° C., under vacuum of 10 mtorr to 760 torr. Then, depending on the n:m target ratio and the final molecular weight desired in the copolymer, an additional amount of sebacic acid and glycerol, in a. 1:1 mole ratio, is added, and the reaction is continued. Useful reaction parameters in this step include reaction temperatures of from 80 to 140° C., under pressures of 10 mtorr to 760 torr, for reaction times of 2–48 hours.

Another specific embodiment of invention copolymers is a grafted terpolymer of citric acid, succinic acid, butanediol, and mPEG. This polymer has the structure.

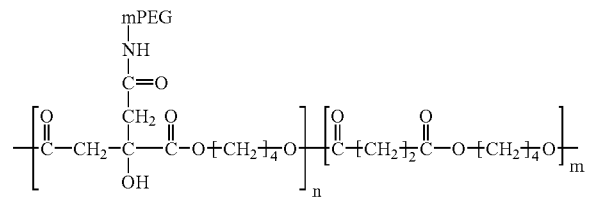

Another specific embodiment of the invention copolymers is a grafted terpolymer of tricarballylic acid, succinic acid, 1,4-butanediol and the monomethyl ether of polyethylene glycol MW=600 (mPEG600). Again, one method of making this polymer is a two-step process where the mPEG is reacted first due to its lower reactivity. Generally, the mPEG is coupled to the tricarballylic acid by coupling an Generally, this type of copolymer can also be synthesized in a two-step process. First, the total amount of adipoyl chloride is added to the reaction vessel under anhydrous conditions with an appropriate amount of pyridine to absorb the released HCl. The solvent is toluene. Next, dry PEG600 is added. After the PEG600 has reacted (which results in a adipoyl-chloride-terminated PEG600), 1,3-propanediol is added. 1,3-propanediol is a breakdown product of all biodegradable polymers containing the monomer trimethylene carbonate. 1,3-propanediol is biocompatible. In various embodiments, the molecular weight of the PEG can be varied, the diol can be varied, and the diacid can be varied. In some embodiments, the diacid is one or more of succinic, adipic, or sebacic acids. In some embodiments, this type of polymer is linear and solvent soluble. It is also possible to make copolymers with both pendant and in-chain biobeneficial moieties. This is particularly true in two-step reaction schemes where two different types of acid terminated, biobeneficial derivatized blocks can be synthesized separately, and then combined and further reacted with additional diacid and diol.

In various embodiments, the molecular weight of the PEG can be varied, the diol can be varied, and the diacid can be varied. In some embodiments, the diacid is one or more of adipic, succinic, and sebacic acid. In some embodiments this type of copolymer is linear and solvent soluble.

In some invention embodiments, the bioactive moiety is selected to have or to also have free-radical scavenging characteristics. Specific examples of useful bioactive moieties that have free-radical scavenging characteristics include superoxide dismutase or a nitric oxide donor.

In addition to being used as a non-fouling coating, invention copolymers may be coated onto a polymeric stent, a metal stent, or a bare metal stent, or they may be coated on top of a drug eluting coating already present on a stent. Alternatively, invention copolymers may be disposed between a stent and a drug-eluting coating. Also, invention copolymers can be used to construct polymer-based medical devices or can serve as the substrate from which medical devices (implantable or not) are constructed.

Invention copolymers can also be used as mixtures with other polymers. For example, invention polymers can be physically blended with PEG, POLYACTIVE(™), or other biobeneficial polymers. These blends could be formulated to modulate biological outcome.

For purposes of this disclsoure, "modulate biological outcome" means adjusting the polymer biobeneficial-component content in order to minimize fibrinogen absorption, platelet binding, the number of adherent macrophages and inflammatory cells, and the degree to which inflammatory cells are activated.

These blends could also be formulated to modulate or tune the release rate of drugs from coatings, reservoirs, or particles composed of these blends and drugs or therapeutic agents. Blends with other polymers can be formulated to modulate the mechanical properties of invention polymers. For instance, other polymers could be blended into invention polymers to modify mechanical properties or vice versa. Useful polymers for preparing such blends include polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), and poly(ester amides).

In some embodiments coatings may be formed on medical devices using invention copolymers as the coating material base. In some embodiments this is accomplished by applying the copolymer of the drugs, polyol(s), and diacid(s) to the surface of the medical device before the copolymer has been substantially crosslinked. Then the coating can be crosslinked slowly by heating the coating. Slow crosslinking is facilitated by the presence of the "third" hydroxyl group, which is a secondary (or tertiary) hydroxyl. Alternatively, a crosslinking step can be carried out simultaneously during sterilization, such as heat or electron-beam sterilization.

Crosslinking (in bulk invention polymer or in coatings comprising invention polymer) can be carried out so that the crosslinks form mainly between invention copolymer chains. Alternatively, the crosslinks can form between invention copolymer chains in blends, or between invention copolymers in one layer and the molecules or polymer chains in primer layers or in other polymer layers.

Conventional therapeutic agents, such as small-hydrophobic drugs, may also be added to invention copolymers, making them bioabsorbable, drug-eluting systems. Conventional therapeutic agents can be grafted on to the invention copolymers or can be mixed in the invention copolymers. Invention copolymers can be coated as blends with a variety of other biobeneficial polymers. Moreover, they can serve as base or topcoat layers for other biobeneficial polymer layers.

The therapeutic agent can be for inhibiting the activity of vascular smooth muscle cells. More specifically, the therapeutic agent can be aimed at inhibiting abnormal or inappropriate migration or proliferation of smooth muscle cells to prevent, inhibit, reduce, or treat restenosis. The therapeutic agent can also include active agent may be any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances as well as combinations thereof. An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck & Co.), monoclonal antibodies (such as PDGF receptors), nitroprusside, phosphodiesterase inhibitors, prostaglandin inhibitor (available form Glazo), Seramin (a PDGF antagonist), serotonin blockers, thioprotease inhibitors, triazolopyrimidine (a PDGF antagonist), and nitric oxide. Other therapeutic substances or agents that may be appropriate include alpha-interferon, genetically engineered epithelial cells, dexamethasone, estradiol, clobetasol propionate, cisplatin, insulin sensitizers, receptor tyrosine kinase inhibitors and carboplatin. Exposure of the composition to the active agent should not adversely alter the active agent's composition or characteristic. Accordingly, the particular active agent is selected for compatibility with the blended composition. Rapamycin is a suitable active agent. Additionally, 40-O-(2-hydroxy)ethyl-rapamycin, or a functional analog or structural derivative thereof, is suitable, as well. Examples of analogs or derivatives of 40-O-(2-hydroxy)ethyl-rapamycin include but are not limited to 40-O-(3-hydroxy)propyl-rapamycin and 40-O-[2-(2-hydroxy)ethoxy]ethyl-rapamycin. The release rate active agents, such as 40-O-(2-hydroxy)ethyl-rapamycin, can be advantageously controlled by various methods and coatings as is known in the art.

As stated above, invention block copolymers can be used with other polymers and biopolymers. Representative examples of polymers useful with invention block copolymers include ethylene vinyl alcohol copolymer, poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Examples of implantable devices for the present invention include self-expandable stents, balloon-expandable stents, stent-grafts, grafts (e.g., aortic grafts), vascular grafts, artificial heart valves, cerebrospinal fluid shunts, pacemaker electrodes, guidewires, ventricular assist devices, artificial hearts, cardiopulmonary by-pass circuits, blood oxygenators, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium, and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

What is claimed is:

1. A polymer with the following formula:

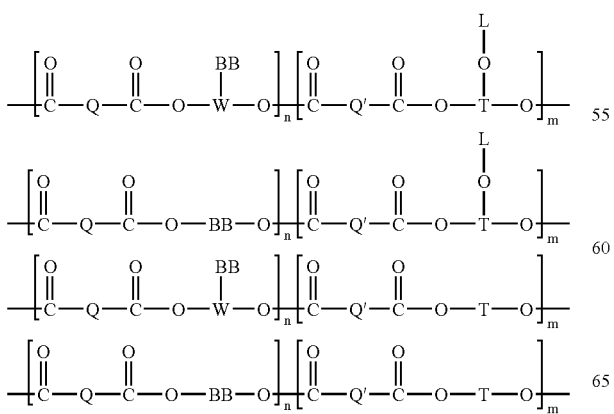

-continued

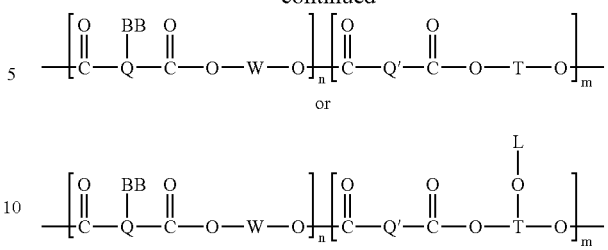

wherein
a) n is 2 to 250;
b) m is 10 to 4500;
c) L represents a crosslinking group or hydrogen;
d) Q and Q' represent the same or different, 1–18 carbon atom hydrocarbon chains;
e) W represents a 1–8 carbon atom hydrocarbon chain;
f) T represents a 1–16 carbon atom hydrocarbon chain; and
g) BB represents a biobeneficial moiety derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonated polystyrene, superoxide dismutase mimetics, anti-oxidants, or free radical scavengers.

2. A medical device comprising a polymer comprising:
a) an alcoholic moiety derived from an aliphatic diol, triol, or polyol;
b) an acidic moiety derived from a polycarboxylic acid; and
c) a biobeneficial moiety derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonated polystyrene, superoxide dismutase mimetics, anti-oxidants, or free radical scavengers,
wherein the polycarboxylic acid is selected from the acidic moiety derived from at least one diacid selected from the group consisting of straight chain aliphatic diacids having 2 to 20 carbon atoms, terephthalic acid, fumaric acid, citric acid, citramalic acid, tricarballylic acid, tartaric acid, isophthalic acid, 1,6-bis(p-carboxy phenoxy)hexane, 1,3-bis(p-phenoxy carboxy)propane, 1,4-bis(p-phenoxy carboxy)butane, and oligomeric diacids with anhydride bonds in the backbone.

3. The medical device of claim 2 wherein the alcoholic moiety is derived from a diol having from 1 to 25 carbon atoms or a saccharide.

4. The medical device of claim 3 wherein the alcoholic moiety is derived from a diol having 1 to 16 carbon atoms.

5. The medical device of claim 2 wherein the alcoholic moiety is derived from at least one of ethylene glycol, 1,2-propane diol, 1,3-propane diol, 1,4-butanediol, 1,5-butanediol, 1,6-hexanediol, 1,7-heptanediol, 1,8-octanediol, higher diols up to C16, glycerol, trimethylol propane, pentaerythritol, cyclohexanedimethanol, serinol, diethanolamine, or saccharides.

6. The medical device of claim 5 wherein saccharides are selected from erythrose, threose, ribose, arabinose, xylose, lyxose, dihydroxyacetone, erythrulose, xylulose, aldoses, or ketoses.

7. The medical device of claim 6 comprising at least three alcoholic moieties derived from an aliphatic diol, triol, or polyol.

8. The medical device of claim 2 wherein the acidic moiety is derived from at least one of oxalic acid, malonic acid, succinic acid, glutaric acid, adipic acid, pimelic acid, suberic acid, azaleic acid, sebacic acid, terephthalic acid, or malic acid.

9. The medical device of claim 2 wherein oligomeric diacids with anhydride bonds in the backbone are selected from poly(sebacic anhydride), poly(suberic anhydride), poly(adipic anhydride), poly(succinic anhydride), poly(maleic anhydride), poly(1,6-bis(p-phenoxy carboxy)hexane), poly(1,4-bis(p-phenoxy carboxy)butane), poly(1,3-bis(p-phenoxy carboxy)propane), and poly(1,4-dicarboxybenzene).

10. The medical device of claim 8 comprising at least two acidic moieties each derived from a different polycarboxylic acid.

11. The medical device of claim 2 wherein the biobeneficial moiety, the non-fouling moiety, or the bioactive moiety are selected such that they give rise to a released molecule that can pass through a mammalian kidney.

12. The medical device of claim 11 wherein the biobeneficial moiety, the non-fouling moiety, or the bioactive moiety are selected such that the released molecule has a molecular weight of less than or equal to 40,000 daltons.

13. The medical device of claim 2 wherein the biobeneficial moiety is at least one of the polypropylene glycol, block polymer surfactants of polyethylene glycol and polypropylene glycol, hydroxy functional poly(vinyl pyrrolidone), dextrin, sodium hyaluronate, heparin, elastin, chitosan, water-soluble derivatives of heparin, water-soluble derivatives of elastin, water-soluble derivatives of chitosan, tropoelastin, poly(2-hydroxyethyl methacrylate), hirudin, or sulfonated polystyrene.

14. The polymer of claim 1 wherein the formula is

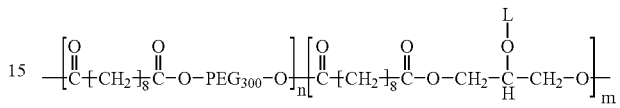

wherein L represents a crosslinking group or hydrogen.

15. The polymer of claim 1 wherein the formula is

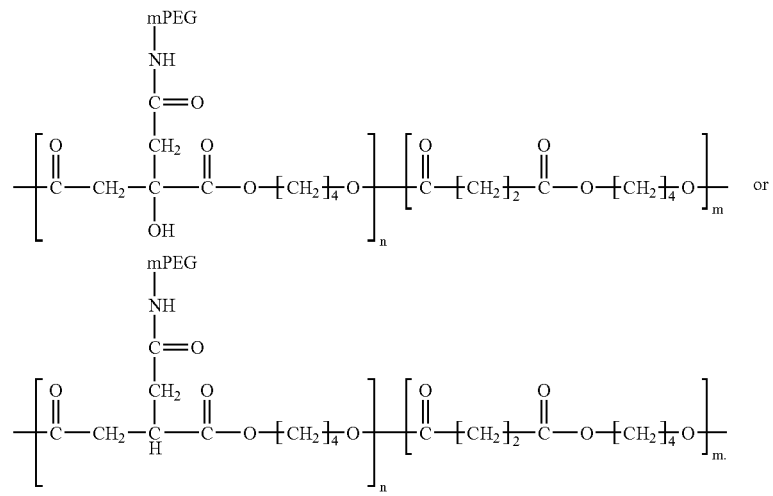

16. The polymer of claim 1 wherein the formula is

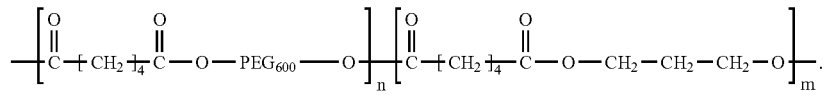

17. A medical device comprising a block copolymer comprising at least two blocks wherein:
   a) the first block comprises a block copolymer comprising:
      i) a first-block alcoholic moiety derived from a di-, tri-, or poly-ol; and
      ii) a first-block acidic moiety derived from a di-, tri-, or poly-acidic carboxylic acid; and
   b) the second block comprises a block copolymer comprising:
      i) a second-block alcoholic moiety derived from a di-, tri-, or poly-ol; and
      ii) a second-block acidic moiety derived from a di-, tri-, or poly-acidic carboxylic acid wherein at least one of the first- or second-block alcoholic moieties or first- or second-block acidic moieties is attached to a biobeneficial moiety derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonared polystyrene, superoxide dismutase mimetics, anti-oxidants, or free radical scavengers.

18. The medical device of claim 17 further comprising a third block comprising a block copolymer comprising:
   a) a third-block alcoholic moiety derived from a di-, tri-, or poly-ol; and
   b) a third-block acidic moiety derived from a di-, tri-, or poly-acidic carboxylic acid.

19. The medical device of claim 17 wherein the first- and the second-block alcoholic constituents are independently derived from 1-to-50-carbon-atom molecules.

20. The medical device of claim 19 wherein the first- and the second-block alcoholic moieties are independently derived from 1-to-10-carbon-atom molecules.

21. The medical device of claim 17 wherein first- and second-block alcoholic moieties are independently derived from at least one of ethylene glycol, 1,2-propane diol, 1,3-propane dial, 1,4-butanediol, 1,5-butanediol, 1,6-hexanediol, 1,7-heptanediol, 1,8-octanediol, higher diols up to $C_{16}$, glycerol, trimethylol propane, pentaerythritol, cyclohexanedimethanol, serinol, diethanolamine, or saccharides.

22. The medical device of claim 21 wherein saccharides are selected from erythrose, threose, ribose, arabinose, xylose, lyxose, dihydroxyacetone, erythrulose, xylulose, aldoses, or ketoses.

23. The medical device of claim 17 wherein the first- and second-block acidic moieties are independently derived from 1-to-50-carbon-atom molecules.

24. The medical device of claim 23 wherein the first- and the second-block acidic moieties are independently derived from 1-to-10-carbon-atom molecules.

25. The medical device of claim 17 wherein the first- and the second-block acidic moieties are independently derived from at least one of oxalic acid, malonic acid, succinic acid, glutaric acid, adipic acid, pimelic acid, suberic acid, azaleic acid, sebacic acid, terephthalic acid, malic acid, fumaric acid, citric acid, citramalic acid, tricarballylic acid, tartaric acid, isophthalic acid, phthalic acid, 1,6-bis(p-carboxy phenoxy)hexane, 1,3-bis(p-phenoxy carboxy)propane, 1,4-bis(p-phenoxy carboxy)butane, dodecanedioic acid, tetradecanedioic acid, hexadecanedioic acid, or oligomeric diacids with anhydride bonds in the backbone.

26. The medical device of claim 25 wherein oligomeric diacids with anhydride bonds in the backbone are selected from poly(sebacic anhydride), poly(suberic anhydride), poly(adipic anhydride), poly(succinic anhydride), poly(maleic anhydride), poly( 1,6-bis(p-phenoxy carboxy)hexane), poly(1,4-bis(p-phenoxy carboxy)butane), poly(1,3-bis(p-phenoxy carboxy)propane), and poly(1,4-dicarboxybenzene).

27. The medical device of claim 17 wherein the biobeneficial molecule is at least one of the polypropylene glycol, block copolymer surfactants of polyethylene glycol and polypropylene glycol, hydroxy functional poly(vinyl pyrrolidone), dextrin, sodium hyaluronate, heparin, elastin, water-soluble derivatives of heparin, water-soluble derivatives of elastin, water-soluble derivatives of chitosan, tropoelastin, poly(2-hydroxyethyl methacrylate), hirudin, or sulfonated polystyrene.

28. A method for preparing the polymer of claim 1 comprising:
   a) preparing a polymerizable biobeneficial moiety based on BB;
   b) polymerizing a polycarboxylic acid based on Q with the polymerizable biobeneficial moiety;
   c) then polymerizing a mixture of a polycarboxylic acid based on Q', a di-, tri-, or polyol based on T, and the product of b).

29. The method of claim 28 wherein preparing a polymerizable biobeneficial moiety based on BB comprises connecting a biobeneficial moiety, BB, to a di-, tri-, or poly-ol based on W.

30. A method for preparing the polymer of claim 1 comprising:
   a) polymerizing a polycarboxylic acid based on Q with the biobeneficial moiety, BB; and
   b) then copolymerizing a polycarboxylic acid based on Q', a di- , tri-, or polyol based on W, and the product of a).

31. A composition comprising a first polymer blended with the polymer of claim 1.

32. The composition of claim 31 wherein the first polymer modulates biological outcome.

33. The composition of claim 31 wherein the first polymer comprises polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3 -hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), or poly(ester amides).

34. The composition of claim 32 wherein the first polymer comprises polycaprolactone, poly(D,L-lactide), poly(L-lactide), poly(D,L-lactide-co-L-lactide), poly(glycolide), poly(D,L-lactide-co-glycol ide), poly(dioxanone), poly(4-hydroxybutyrate), poly(3-hydroxybutyrate), poly(3 -hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), or poly(ester amides).

35. A polymer with the following formula:

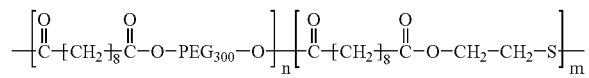

wherein S represents sulfur, n is 2 to 250, and m is 10 to 4500.

36. A polymer comprising:
   an alcoholic moiety derived from an aliphatic diol having from 1 to 25 carbon atoms or a saccharide;
   an acidic moiety derived from a polycarboxylic acid; and
   a biobeneficial moiety is derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonated polystyrene, superoxide dismutase mimetics, anti-oxidants, or free radical scavengers, wherein the polycarboxylic acid is selected from the acidic moiety derived from at least one diacid selected from the group consisting of straight chain aliphatic diacids having 2 to 20 carbon atoms, terephthalic acid, fumaric acid, citric acid, citramalic acid, tricarballylic acid, tartaric acid, isophthalic acid, 1,6-bis(p-carboxy phenoxy)hexane, 1,3-bis(p-phenoxy carboxy)propane, 1,4-bis(p-phenoxy carboxy)butane, and oligomeric diacids with anhydride bonds in the backbone.

37. A polymer comprising:
an alcoholic moiety derived from an aliphatic diol, triol, or polyol;
an acidic moiety derived from a polycarboxylic acid; and
a biobeneficial moiety having biobeneficial characteristics, a non-fouling moiety having non-fouling characteristics, a bioactive moiety having bioactive characteristics, or a moiety that has any combination of biobeneficial, non-fouling, or bioactive characteristics, wherein the biobeneficial moiety is derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonated polystyrene, superoxide dismutase mimetics, anti-oxidants, or free radical scavengers, and wherein the polycarboxylic acid is selected from the acidic moiety is derived from at least one diacid selected from the group consisting of straight chain aliphatic diacids having 2 to 20 carbon atoms, terephthalic acid, fumaric acid, citric acid, citramalic acid, tricarballylic acid, tartaric acid, isophthalic acid, 1,6-bis(p-carboxy phenoxy)hexane, 1,3-bis (p-phenoxy carboxy)propane, 1,4-bis(p-phenoxy carboxy)butane, and oligomeric diacids with anhydride bonds in the backbone.

38. A polymer comprising:
an alcoholic moiety derived from an aliphatic diol, triol, or polyol;
an acidic moiety derived from a polycarboxylic acid; and
a biobeneficial moiety is derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonated polystyrene, superoxide dismutase mimetics, anti-oxidants, or free radical scavengers having a molecular weight of less than or equal to 40,000 daltons, wherein the polycarboxylic acid is selected from the acidic moiety is derived from at least one diacid selected from the group consisting of straight chain aliphatic diacids having 2 to 20 carbon atoms, terephthalic acid, fumaric acid, citric acid, citramalic acid, tricarballylic acid, tartaric acid, isophthalic acid, 1,6-bis(p-carboxy phenoxy)hexane, 1,3-bis(p-phenoxy carboxy)propane, 1,4-bis(p-phenoxy carboxy)butane, and oligomeric diacids with anhydride bonds in the backbone.

39. A block copolymer comprising at least two blocks wherein:
a) the first block comprises a block copolymer comprising:
i) a first-block alcoholic moiety independently derived from at least one of ethylene glycol, 1,2-propane diol, 1,3-propane diol, 1,4-butanediol, 1,5-butanediol, 1,6-hexanediol, 1,7-heptanediol, 1,8-octanediol, higher diols up to C16, glycerol, trimethylol propane, pentaerythritol, cyclohexanedimethanol, serinol, diethanolamine, or saccharides; and
ii) a first-block acidic moiety derived from a di-, tri-, or poly-acidic carboxylic acid; and
b) the second block comprises a block copolymer comprising:
i) a second-block alcoholic moiety independently derived from at least one of ethylene glycol, 1,2-propane diol, 1,3-propane diol, 1,4-butanediol, 1,5-butanediol, 1,6-hexanediol, 1,7-heptanediol, 1,8-octanediol, higher diols up to C16, glycerol, trimethylol propane, pentaerythritol, cyclohexanedimethanol, serinol, diethanolamine, or saccharides; and
ii) a second-block acidic moiety derived from a di-, tri-, or poly-acidic carboxylic acid;
wherein at least one of the first- or second-block alcoholic moieties or first- or second-block acidic moieties is attached to a biobeneficial moiety derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin, poly(2-hydroxyethyl methylmethacrylate), heparin, hirudin, sulfonated polystyrene, superoxide dismutase mimetics, anti-oxidants, or free radical scavengers.

40. The copolymer of claim 39 wherein saccharides are selected from erythrose, threose, ribose, arabinose, xylose, lyxose, dihydroxyacetone, erythrulose, xylulose, aldoses, or ketoses.

41. A composition comprising:
a first polymer, wherein the first polymer comprises polycaprolactone, poly(D,L-lactide), poly(L-lactide), poly(D,L-lactide-co-L-lactide), poly(glycolide), poly (D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly (trimethylene carbonate), poly(anhydrides), poly (orthoesters), or poly(ester amides), blended with
a second polymer, wherein the second polymer comprises
an alcoholic moiety derived from an aliphatic diol, triol, or polyol;
an acidic moiety derived from a polycarboxylic acid; and
a biobeneficial moiety derived from polypropylene glycol, PLURONIC™ surfactants, block copolymers comprising polyethylene glycol and polypropylene glycol, hydroxy functional poly(vinyl pyrrolidone), dextrin, sodium hyaluronate, hyaluronic acid, elastin, water-soluble heparin, water-soluble elastin, tropoelastin poly (2-hydroxyethyl methylmethacrylate), heparin, hirudin, sulfonated polystyrene, superoxide dismutase mimetics, anti-oxidants, or free radical scavengers.

42. The composition of claim 41 wherein the first polymer modulates biological outcome.

* * * * *